(12) United States Patent
Saito

(10) Patent No.: US 11,596,290 B2
(45) Date of Patent: Mar. 7, 2023

(54) IMAGE PICKUP SYSTEM, ENDOSCOPE SYSTEM, AND IMAGE PICKUP GAIN SETTING METHOD

(71) Applicant: OLYMPUS CORPORATION, Tokyo (JP)

(72) Inventor: Saeri Saito, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 334 days.

(21) Appl. No.: 16/717,448

(22) Filed: Dec. 17, 2019

(65) Prior Publication Data

US 2020/0121174 A1 Apr. 23, 2020

Related U.S. Application Data

(63) Continuation of application No. PCT/JP2018/009790, filed on Mar. 13, 2018.

(30) Foreign Application Priority Data

Jun. 29, 2017 (JP) .............................. JP2017-127324

(51) Int. Cl.
*A61B 1/00* (2006.01)
*A61B 1/04* (2006.01)
(Continued)

(52) U.S. Cl.
CPC .......... *A61B 1/00009* (2013.01); *A61B 1/043* (2013.01); *A61B 1/045* (2013.01); *G02B 23/24* (2013.01)

(58) Field of Classification Search
CPC ..... A61B 1/00009; A61B 1/043; A61B 1/045; A61B 1/0638; H04N 5/235; H04N 5/243;
(Continued)

(56) References Cited

U.S. PATENT DOCUMENTS

2005/0203343 A1 9/2005 Kang et al.
2014/0354788 A1* 12/2014 Yano ...................... A61B 1/045
348/68
(Continued)

FOREIGN PATENT DOCUMENTS

EP 3 190 785 A1 7/2017
JP 2011-250925 A 12/2011
(Continued)

OTHER PUBLICATIONS

International Search Report dated Jun. 12, 2018 received in PCT/JP2018/009790.

*Primary Examiner* — Aaron B Fairchild
*Assistant Examiner* — Julianna J Nicolaus
(74) *Attorney, Agent, or Firm* — Scully, Scott, Murphy & Presser, P.C.

(57) ABSTRACT

An image pickup system includes an image pickup device including an image pickup section, a first amplifier circuit capable of amplifying a video signal for each field, and a communication circuit configured to acquire a set gain of the first amplifier circuit, a second amplifier circuit configured to amplify the video signal outputted from the image pickup device, and a processor. According to a result of a detection indicating that the video signal is not amplified by the set gain in the first amplifier circuit, a correction gain to be set in the second amplifier circuit is calculated.

12 Claims, 9 Drawing Sheets

(51) Int. Cl.
*A61B 1/045* (2006.01)
*G02B 23/24* (2006.01)

(58) Field of Classification Search
CPC ............. H04N 5/52; H04N 2005/2255; G02B 23/2461
See application file for complete search history.

(56) References Cited

U.S. PATENT DOCUMENTS

2015/0083895 A1* 3/2015 Hashimoto ............ H04N 5/243 250/208.1
2016/0345812 A1 12/2016 Ogasawara

FOREIGN PATENT DOCUMENTS

| JP | 2011250925 A | * | 12/2011 | | |
|----|--------------|---|---------|---|---|
| JP | 2014-233533 A | | 12/2014 | | |
| WO | 2016/035829 A1 | | 3/2016 | | |
| WO | WO-2016035829 A1 | * | 3/2016 | ........... | H04N 5/3532 |

\* cited by examiner

IMAGE PICKUP SYSTEM, ENDOSCOPE SYSTEM, AND IMAGE PICKUP GAIN SETTING METHOD

CROSS REFERENCE TO RELATED APPLICATION

This application is a continuation application of PCT/JP2018/009790 filed on Mar. 13, 2018 and claims benefit of Japanese Application No. 2017-127324 filed in Japan on Jun. 29, 2017, the entire contents of which are incorporated herein by this reference.

BACKGROUND OF INVENTION

1. Field of the Invention

The present invention relates to an image pickup system, and endoscope system, and an image pickup gain setting method suitable for a fluorescence observation.

2. Description of the Related Art

In recent years, a diagnosis method for discriminating presence or absence of a lesioned part based on autofluorescence emitted from a tissue or fluorescence emitted from a target part of a living body after spraying or injection of a fluorescent agent to the target part has been sometimes adopted. In an endoscope apparatus, diagnosis by a fluorescence observation using this technique is possible. In other words, excitation light emitted from a light source apparatus is irradiated on an object from an insertion section of an endoscope and fluorescence emitted from a fluorescent agent accumulated in a lesioned part is captured by an image pickup device provided in the endoscope to perform presence diagnosis for the lesioned part and qualitative diagnosis for malignancy and the like.

Incidentally, in the fluorescence observation, excitation light for generating fluorescence from a lesioned part is irradiated on a biological tissue and reference light for visualizing a structure and a form of the biological tissue is irradiated on the biological tissue. Confirmation of the lesioned part and the like is facilitated by a combined image (hereinafter referred to as fluorescence observation image) obtained by combining a fluorescence image generated based on the fluorescence obtained by the excitation light and a background image generated based on background light obtained when the reference light reflects on an object.

However, intensity (a light amount) of the fluorescence obtained by the excitation light is small compared with intensity (a light amount) of the background light obtained by the reference light. Therefore, adjustment is performed not only to reduce an emitted light amount of the reference light compared with an emitted light amount of the excitation light in a light source apparatus but also to set levels (brightness) of the fluorescence image and the background image to proper levels in an image pickup device that receives the fluorescence and the background light and performs photoelectric conversion.

For example, when a CCD is adopted as the image pickup device, excess electric charges are discarded during background light reception and brightness of the background image is reduced using an electronic shutter (a charge reset function) to obtain a clear fluorescence observation image.

A CMOS sensor of a rolling shutter type is sometimes adopted as the image pickup device. In the rolling shutter type, reset, exposure, and readout are performed at different timing for each line and, when the readout is performed in a certain line, the exposure is performed in another line. On the other hand, in the fluorescence observation, a method of irradiating the excitation light and the reference light on the biological tissue in a time division manner is sometimes adopted. When such an illumination method is performed in a readout period of the CMOS sensor of the rolling shutter type, a problem such as color mixture occurs. Therefore, when the CMOS sensor of the rolling shutter type is adopted in the fluorescence observation, the exposure is performed in a period other than the readout period. In this case, if the electronic shutter (the charge reset function) is used, unevenness of brightness occurs because timing when electric charges are reset is different for each line. Therefore, when the CMOS sensor of the rolling shutter type is used, gains of the fluorescence image and the background image are adjusted by an amplifier in the image pickup device rather than the electronic shutter.

Note that Japanese Patent Application Laid-Open Publication No. 2014-233533 discloses a technique for alternately irradiating white light and narrow band light in units of one frame and updating and setting an amplification factor of an amplifier for each field.

Incidentally, in general, when a reduction in a diameter of an endoscope insertion section is considered, an image pickup device is disposed at a distal end of the insertion section and a substrate mounted with an electronic circuit for driving the image pickup device is disposed in an operation section, a connector section, or the like connected to a proximal end side of the insertion section. An electronic shutter of the image pickup device and a control circuit for adjusting a gain are mounted on the substrate. A control signal is transmitted to the image pickup device via a signal line wired from the control circuit to the image pickup device.

When a CCD is adopted as the image pickup device and control by the electronic shutter is performed as explained above, a high-voltage analog signal is transmitted from the control circuit as a control signal. The CCD is thus excellent in a noiseproof property. On the other hand, when a CMOS sensor is adopted, information (a gain setting value) for the gain adjustment is transmitted from the control circuit to the image pickup device as digital communication.

However, the endoscope is sometimes used under an environment in which disturbance of communication occurs. For example, during use of an electric knife to which high-frequency current is fed, communication between the control circuit and the image pickup device is likely to be adversely affected by disturbance. A gain setting value from the control circuit is erroneously detected in the image pickup device because of such disturbance. Accurate gain control is not performed in some case.

If error detection is performed using a checksum, a parity, a CRC, or the like generally used in digital communication, the gain setting value is not updated by a wrong gain setting value. Therefore, when gain adjustment is performed for dimming (brightness control corresponding to an object) performed during a normal light observation or the like, a slight delay is caused in the brightness control by occurrence of disturbance.

SUMMARY OF THE INVENTION

An image pickup system according to an aspect of the present invention includes: an image pickup device including an image pickup section configured to pick up an image of an object and output a video signal, a first amplifier circuit capable of amplifying and outputting the video signal for each field, and a communication circuit configured to acquire, through communication with an outside, a set gain to be set as a gain of the first amplifier circuit; an image-pickup control circuit configured to transmit, through communication with the communication circuit, the set gain for each field to the image pickup device; a second amplifier circuit configured to amplify the video signal outputted from the image pickup device; and a processor. The image-pickup control circuit or the processor detects whether the video signal is amplified by the set gain in the first amplifier circuit. The image-pickup control circuit or the processor calculates, according to a result of the detection indicating that the video signal is not amplified by the set gain in the first amplifier circuit, a correction gain set in the second amplifier circuit.

An endoscope system according to an aspect of the present invention is an endoscope system including an endoscope, a light source apparatus capable of irradiating, on an object, illumination light having a different wavelength for each field, and a video processor configured to perform image processing on a video signal outputted from the endoscope, the endoscope system including: an image pickup device including an image pickup section provided in the endoscope and configured to pick up an image of the object and output a video signal, a first amplifier circuit capable of amplifying and outputting the video signal for each field, and a communication circuit configured to acquire, through communication with an outside, a set gain to be set as a gain of the first amplifier circuit; an image-pickup control circuit configured to transmit, through communication with the communication circuit, the set gain for each field to the image pickup device; a second amplifier circuit configured to amplify the video signal outputted from the image pickup device; and a processor. The image-pickup control circuit or the processor detects whether the video signal is amplified by the set gain in the first amplifier circuit. The image-pickup control circuit or the processor calculates, according to a result of the detection indicating that the video signal is not amplified by the set gain in the first amplifier circuit, a correction gain set in the second amplifier circuit.

An image-pickup gain setting method according to an aspect of the present invention is an image-pickup gain setting method for an image pickup system, the image pickup system including: an image pickup device including an image pickup section configured to pick up an image of an object and output a video signal, a first amplifier circuit capable of amplifying and outputting the video signal for each field, and a communication circuit configured to acquire, through communication with an outside, a set gain to be set as a gain of the first amplifier circuit; an image-pickup control circuit configured to transmit, through communication with the communication circuit, the set gain for each field to the image pickup device; and a second amplifier circuit configured to amplify the video signal outputted from the image pickup device, the image-pickup gain setting method including: setting, in the first amplifier circuit, the set gain for each field transmitted from the image-pickup control circuit to the communication circuit; acquiring an actual gain of the first amplifier circuit based on the video signal outputted from the image pickup device; comparing the set gain and the actual gain; calculating, when the set gain and the actual gain do not coincide with each other, a correction gain based on a difference between the actual gain and the set gain; and setting the correction gain in the second amplifier circuit.

DETAILED DESCRIPTION OF THE PREFERRED EMBODIMENTS

Embodiments of the present invention are explained in detail below with reference to the drawings.

First Embodiment

Figure 1:
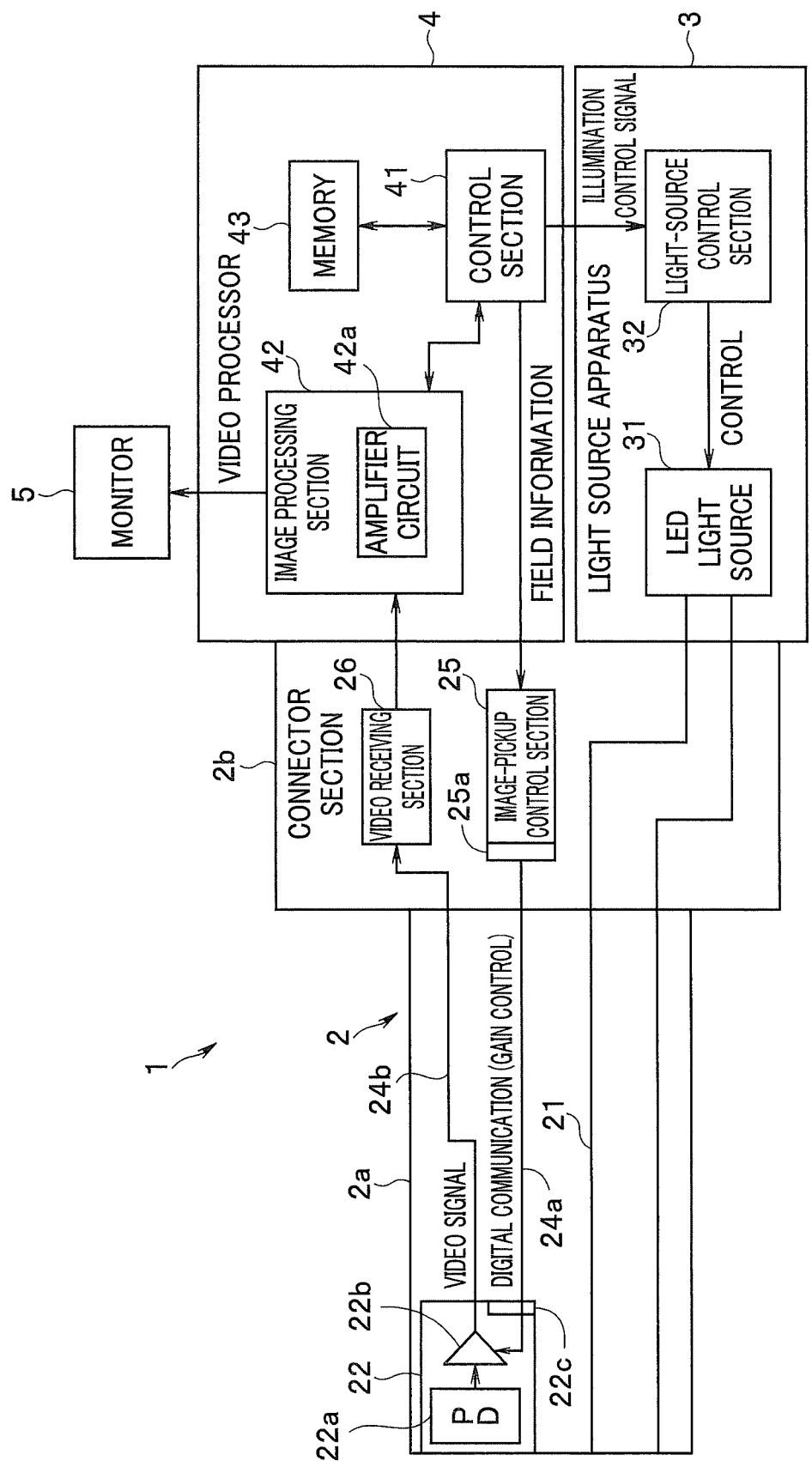
FIG. 1 is a block diagram showing an endoscope system including an image pickup system according to a first embodiment of the present invention.

FIG. 1 is a block diagram showing an endoscope system including an image pickup system according to a first embodiment of the present invention.

In the present embodiment, information concerning a gain actually imparted to outputs of respective pixels by an image pickup device (hereinafter referred to as actual gain) is acquired to calculate, as a correction gain, a difference between the actual gain and a gain to be imparted to the outputs of the respective pixels by the image pickup device (hereinafter referred to as set gain) and the correction gain is imparted to an image pickup device output to obtain video signals at proper levels in respective fields. Note that, in the present embodiment, an example of a fluorescence observation mode in an endoscope system that irradiates excitation light or reference light for each of the fields is explained. However, the present invention can be applied to various operation modes of an image pickup system capable of setting a gain for each of the fields. The operation modes include a frame-sequential mode, a special observation mode such as NBI, and an infrared (IR) observation mode but are not limited to these modes.

In FIG. 1, an endoscope system 1 includes an endoscope 2 inserted into a subject and configured to pick up an image of an object such as a biological tissue in the subject and output the image as a video signal, a light source apparatus 3 configured to supply illumination light for illuminating the object to the endoscope 2, a video processor 4 configured to apply signal processing to the video signal outputted from the endoscope 2 to thereby generate and output a fluorescence observation image or the like, and a monitor 5 configured to display the fluorescence observation image or the like outputted from the video processor 4 on a screen.

The endoscope 2 includes an elongated insertion section 2a inserted into a body cavity of the subject. A not-shown operation section is connected to a proximal end of the insertion section 2a. A connector section 2b is provided at an end portion of a not-shown cable extended from the operation section. The endoscope 2 and the light source apparatus 3 and the video processor 4 are connected via the connector section 2b.

The light source apparatus 3 includes an LED light source 31 and a light-source control section 32. The LED light source 31 is configured by a not-shown white LED for normal observation, a not-shown LED for reference light, and a not-shown LED for excitation light. The light source apparatus 3 is controlled by the light-source control section 32 to perform lighting and extinction of the LED for reference light and the LED for excitation light according to a normal observation mode or a fluorescence observation mode. A light emission amount of the LED light source 31 is controlled by the light-source control section 32. The light-source control section 32 selects a type of illumination light (emitted light) emitted from the LED light source 31 and controls light emission timing and a light emission amount based on an illumination control signal outputted from the control section 41. The illumination light emitted from the LED light source 31 is emitted to a light guide 21.

Note that, in the LED light source 31, LEDs of three colors or R, G, and B may be adopted instead of the white LED for irradiating white light. A combination light source of a lamp of Xe or the like for generating white light and a color filter may be adopted instead of the LED light source 31. The LEDs for the three colors and the combination light source may be combined.

During the fluorescence observation mode, the light-source control section 32 controls the LED light source 31 to emit reference light and excitation light for each of predetermined fields in a time division manner. For example, the light-source control section 32 may control the LED light source 31 to emit the excitation light within a period of two fields among three fields and emit the reference light within a period of the remaining one field.

The light guide 21 for transmitting the illumination light is inserted through an inside of the insertion section 2a of the endoscope 2. An emission end portion of the light guide 21 is disposed at a distal end portion of the insertion section 2a. The light guide 21 leads the illumination light emitted from the light source apparatus 3 to a distal end side of the insertion section 2a and irradiates the illumination light on the subject via a not-shown illumination lens provided at the distal end portion of the insertion section 2a.

A not-shown objective lens is provided at the distal end portion of the insertion section 2a. Return light from the subject is made incident, via the objective lens, on a photoelectric conversion section (PD) 22a of the image pickup device 22 provided on the distal end side of the insertion section 2a. The photoelectric conversion section 22a functioning as an image pickup section converts an object optical image made incident on an image pickup surface into a video signal through photoelectric conversion and outputs the video signal. The output of the photoelectric conversion section 22a is supplied to an amplifier 22b functioning as a first amplifier circuit. The image pickup device 22 includes a communication section 22c configured by a communication circuit. The communication section 22c is configured to be communicable with a communication section 25a of an image-pickup control section 25 functioning as an image-pickup control circuit via a signal line 24a. The communication section 22c receives a gain control signal supplied from the image-pickup control section 25 via the signal line 24a and supplies information concerning a gain included in the gain control signal to the amplifier 22b and sets the gain. The amplifier 22b amplifies, with the set gain, the video signal outputted from the photoelectric conversion section 22a and outputs the video signal. The video signal outputted from the image pickup device 22 is given to a video receiving section 26 via a signal line 24b.

When the image pickup device 22 performs an analog output, the video receiving section 26 applies correlated double sampling processing to an analog video signal outputted from the image pickup device 22 and removes noise. The video receiving section 26 converts the video signal, from which the noise is removed, into a digital signal with analog/digital conversion processing and outputs the digital signal to an image processing section 42 of the video processor 4.

When the image pickup device 22 performs a digital output, the video receiving section 26 receives a digital video signal outputted from the image pickup device 22 and outputs the digital video signal to the image processing section 42 of the video processor 4.

Note that the video receiving section 26 and the image-pickup control section 25 explained below may be configured by an FPGA (field programmable gate array) or may be configured by a processor such as a CPU and configured to control the respective sections according to programs stored in a not-shown memory.

A control section 41 that controls the respective sections is provided in the video processor 4. The control section 41 may be configured by an FPGA (field programmable gate array) or may be configured by a processor such as a CPU and configured to control the respective sections according to programs stored in a not-shown memory.

The image processing section 42 includes an amplifier circuit 42a. The amplifier circuit 42a applies amplification processing to an inputted video signal. The image processing section 42 applies various kinds of signal processing such as color signal processing for generating a color signal, gamma correction processing, electronic zoom processing, and white balance (W/B) processing to the video signal after the amplification, converts the video signal into a display form suitable for the monitor 5, and outputs the video signal to the monitor 5. An endoscopic image (a fluorescence observation image or the like) picked up by the image pickup device 22 is displayed on a display screen of the monitor 5.

During the fluorescence observation, the control section 41 controls the light-source control section 32 with the illumination control signal to emit the excitation light and the reference light from the LED light source 31 at a predetermined field cycle and sufficiently reduce a light amount of the reference light compared with a light amount of the excitation light.

The control section 41 supplies field information for setting a gain of the image pickup device 22 to the image-pickup control section 25. The field information indicates a field in which fluorescence based on the excitation light is made incident on the image pickup device 22 (hereinafter referred to as fluorescence field) or a field in which background light based on the reference light is made incident on the image pickup device 22 (hereinafter referred to as background light field) and includes information concerning gains that the amplifier 22b should impart in the respective fields (set gains). The information concerning the set gains is stored in a memory 43. The control section 41 reads out the information stored in the memory 43 to acquire the information concerning the set gain of the fluorescence field and the information concerning the set gain of the background light field and transmits the information to the image-pickup control section 25 with the field information.

Note that the set gain of the fluorescence field is set to a sufficiently large gain compared with the set gain of the background light field.

The image-pickup control section 25 outputs a gain control signal for designating the set gains to the communication section 22c through digital communication performed via the signal line 24a. The communication section 22c sets the received set gains in the amplifier 22b. Consequently, the amplifier 22b amplifies the video signal outputted from the photoelectric conversion section 22a with gains conforming to the set gains in the respective fields and outputs the video signal.

Note that not only gains set in the respective fields are different for each of the fields during the fluorescence observation mode but also gains set in the respective fields are different during the normal observation mode and during the fluorescence observation mode. Therefore, the memory 43 is configured to store information concerning set gains for each of the respective modes. The control section 41 reads out the set gains corresponding to types of modes and fields and notifies the set gains with the field information.

In this case, the control section 41 may be configured to notify the field information for each of the fields. The control section 41 may be configured to, when a delay occurs in the reception of the field information and the gain setting in the endoscope 2, transmit the field information earlier by the delay. Alternatively, the control section 41 may collectively notify which set gains are to be used in the respective fields. For example, the control section 41 may be configured to notify values of the respective set gains of the fluorescence field and the background light field in advance and notify field information indicating, for each of the fields, only the field, whereby the image-pickup control section 25 may set the set gain for each of the fields in the amplifier 22b.

The amplifier 22b amplifies video signals using the set gains set in the respective fields and outputs the video signal, whereby levels of a video signal based on the fluorescence supplied to the video receiving section 26 (hereinafter, fluorescence video signal) and a video signal based on the background light (hereinafter, background video signal) are made proper. Consequently, a fluorescence observation image based on these video signals becomes a clear image.

However, in some case, the set gains are not transmitted or wrong set gains are transmitted because of occurrence of disturbance. Consequently, in some case, for example, gains unrelated to the set gains are set in the amplifier 22b or the set gain of the fluorescence field is set in the amplifier 22b as the set gain of the background light field. Conversely, the set gain of the background light field is set in the amplifier 22b as the set gain of the fluorescence field or the set gain is not transmitted and a gain of a preceding field that should be changed is directly set in the amplifier 22b and amplification is performed.

Therefore, in the present embodiment, the information concerning the actual gain is acquired to determine whether the set gains are set and, when the set gains are not set, control for imparting gains equivalent to the set gains is performed to obtain a fluorescence video signal and a background video signal in the same levels as levels at the time when the set gains are imparted.

(Acquiring Method for the Actual Gain)

For example, the image pickup device 22 can embed, in a vertical blanking period or a horizontal blanking period of a video signal, information concerning a gain value (an actual gain) imparted to the video signal and output the video signal. The video receiving section 26 acquires the information concerning the actual gain from the received video signal. The video receiving section 26 may be configured to directly transmit the acquired information concerning the actual gain to the control section 41 of the video processor 4. For example, the video receiving section 26 may embed the information concerning the actual gain in the vertical blanking period or the horizontal blanking period of the video signal transmitted to the image processing section 42 of the video processor 4 and thereafter transmit the video signal. In this case, the image processing section 42 is configured to give the information concerning the actual gain acquired from the video signal to the control section 41.

For example, the video receiving section 26 may be configured to supply the information concerning the actual gain to the control section 41 of the video processor 4 via a not-shown communication line different from a communication line for the video signal.

When the actual gain is not set because of a communication failure due to the signal line 24a, the actual gain is sometimes a set gain of a preceding field. The video receiving section 26 may be configured to transmit only information concerning whether the actual gain coincides with the set gain to the video processor 4 in this case.

The video receiving section 26 may be configured to, for example, receive the information concerning the set gain from the control section 41 of the video processor 4. In this case, the video receiving section 26 may calculate a correction gain based on the information concerning the set gain and the information concerning the actual gain. For example, the video receiving section 26 may calculate a difference between the set gain and the actual gain as the correction gain and transmit information concerning the correction gain to the video processor 4.

Besides a method of calculating the actual gain with the video receiving section 26, a method of calculating the actual gain with the image-pickup control section 25 can also be adopted. The image-pickup control section 25 may be configured to acquire, through digital communication performed via the signal line 24a with the communication section 22c of the image pickup device 22, the information concerning the actual gain imparted by the amplifier 22b. In this case, the image-pickup control section 25 transmits the acquired information concerning the actual gain to the control section 41 of the video processor 4. The image-pickup control section 25 may be configured to output information concerning consistency or inconsistency of the actual gain and the set gain to the control section 41. The image-pickup control section 25 may be configured to calculate the correction gain and output the calculated correction gain to the control section 41.

The control section 41 reads out the information concerning the set gain from the memory 43, determines whether the actual gain and the set gain are different, and, when the actual gain and the set gain are different, calculates a difference between the actual gain and the set gain and gives the difference to the image processing section 42 as the correction gain. The image processing section 42 sets the given correction gain in the amplifier circuit 42a and imparts the correction gain to the video signal outputted from the video receiving section 26.

In other words, the image-pickup control section 25, the video receiving section 26, and the control section 41 configure, independently or in combination, a processor having functions of a detecting section that detects whether the set gain is imparted to the video signal in the amplifier 22b and a correction-gain acquiring section that acquires the correction gain.

Note that when receiving, from the image pickup device 22, information indicating that the set gain and the actual gain do not coincide with each other, the image processing section 42 may request the control section 41 to supply the information concerning the correction gain. The control section 41 supplies, to the image processing section 42, a correction gain corresponding to which field the video signal inputted to the image processing section 42 belongs to. The amplifier circuit 42a amplifies the inputted video signal using the correction gain.

When the information concerning the correction gain is given from the video receiving section 26, the image processing section 42 performs, with the amplifier circuit 42a, amplification on the inputted video signal using the received correction gain.

Note that the control section 41 is configured to set, when the information concerning the actual gain, the information concerning consistency or inconsistency of the actual gain and the set gain, or the information concerning the correction gain is supplied from the image-pickup control section 25 to the control section 41, the correction gain in the image processing section 42 based on these kinds of information.

In the case of the set gain—the actual gain >0, the amplifier circuit 42a imparts a correction gain having an amplification factor larger than 1 to the video signal. In the case of the set gain—the actual gain <0, the amplifier circuit 42a imparts a correction gain having an amplification factor smaller than 1 to the video signal. The correction gain is calculated based on a difference between the actual gain and the set gain. Gains equivalent to the set gain are imparted to the video signals in the respective fields. The video signals in the respective fields are amplified to appropriate levels.

Note that, in an example shown in FIG. 1, the digital video signal is outputted from the endoscope 2. The amplifier circuit 42a of the image processing section 42 performs amplification with the digital processing. However, when an analog video signal is outputted from the endoscope 2, the correction gain only has to be imparted by analog processing.

Figure 2:
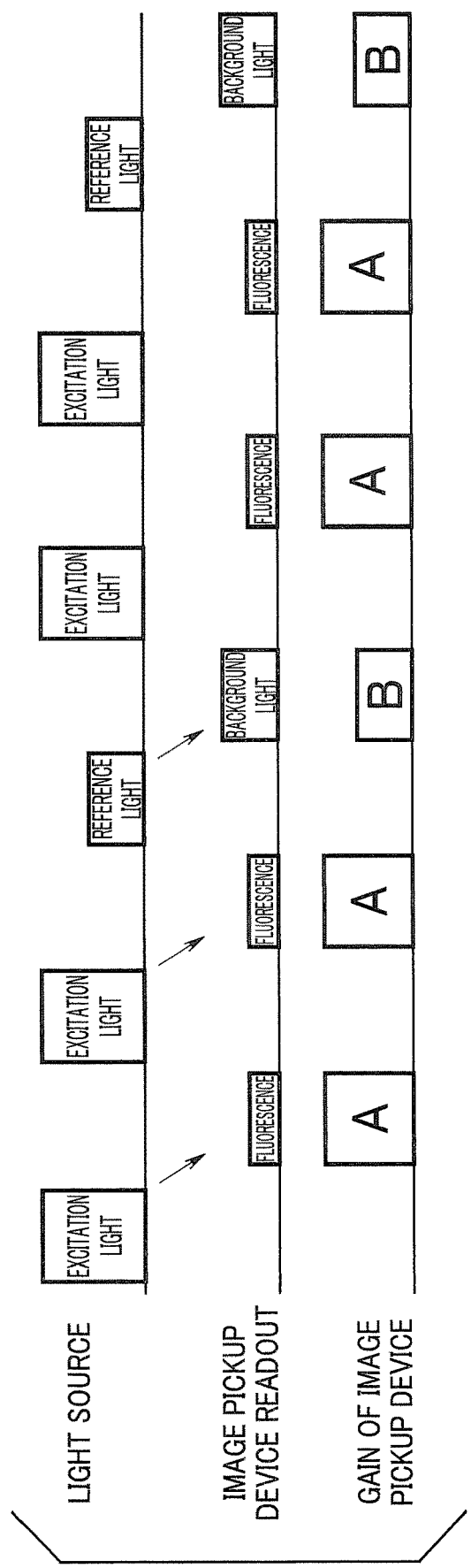
FIG. 2 is an explanatory diagram for explaining a set gain.
Figure 3:
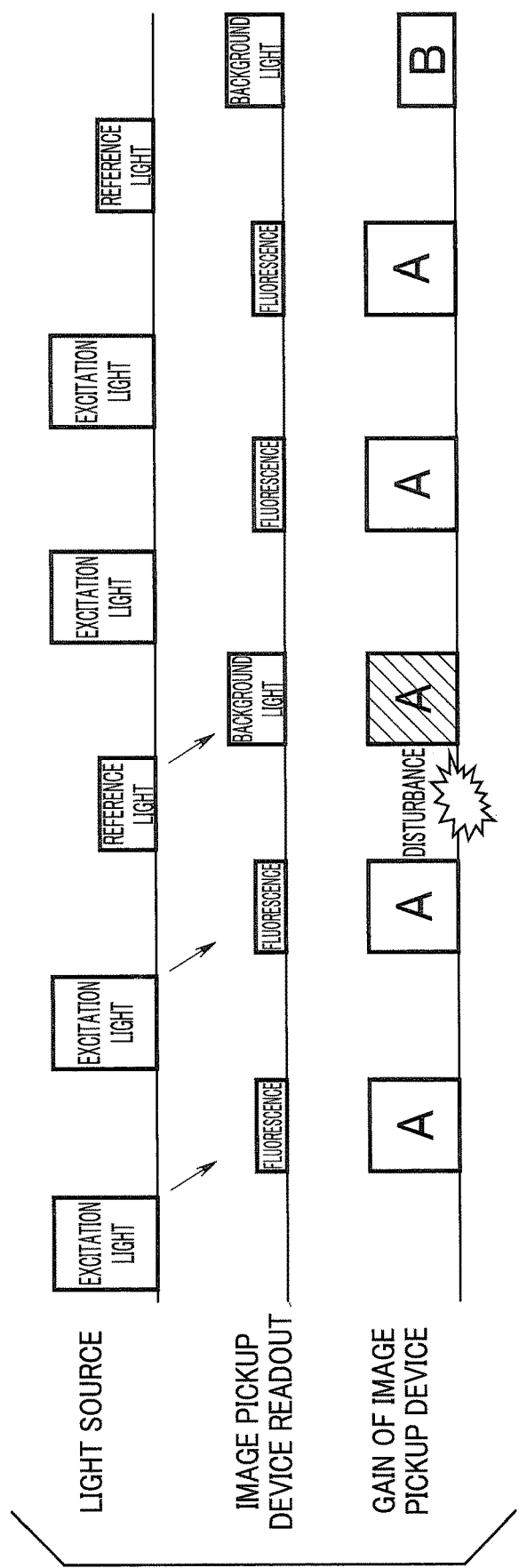
FIG. 3 is an explanatory diagram for explaining an actual gain during disturbance occurrence.
Figure 4:
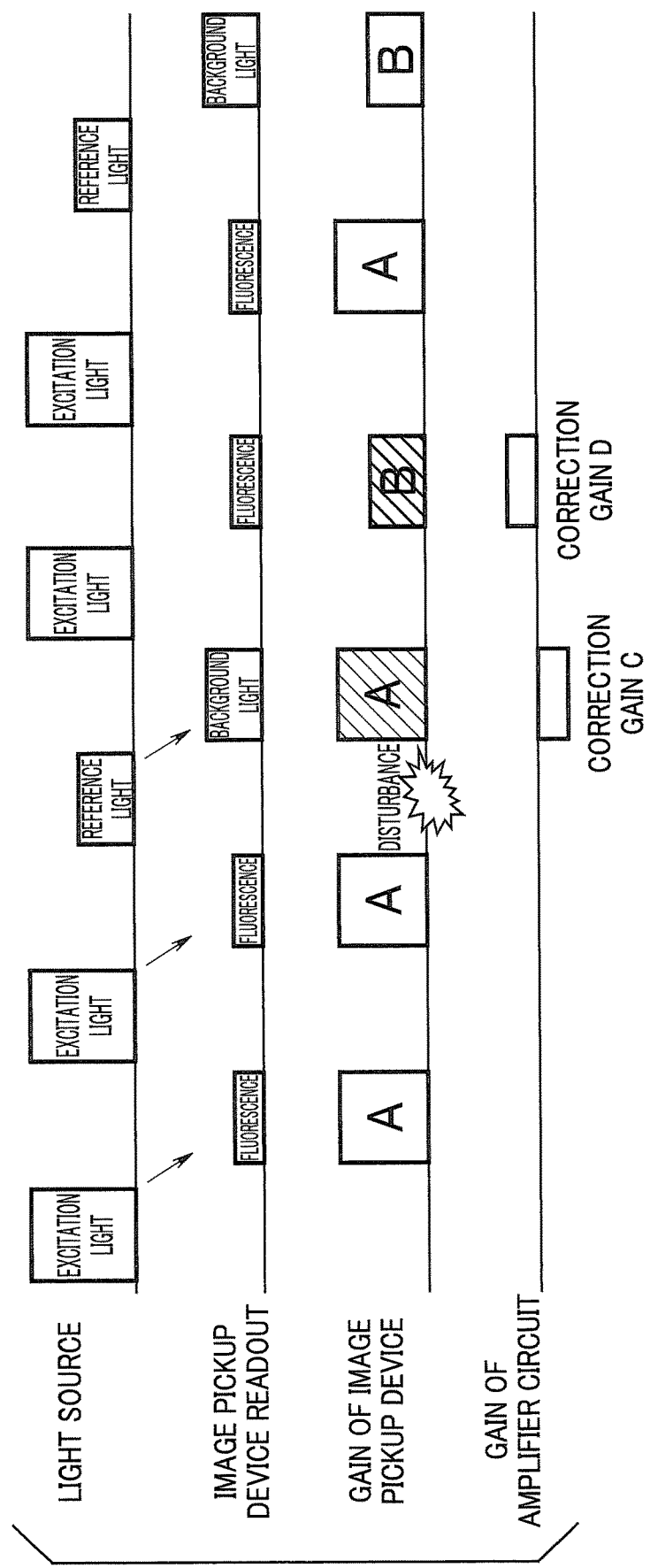
FIG. 4 is an explanatory diagram showing an example in which a correction gain is imparted during the disturbance occurrence.
Figure 5:
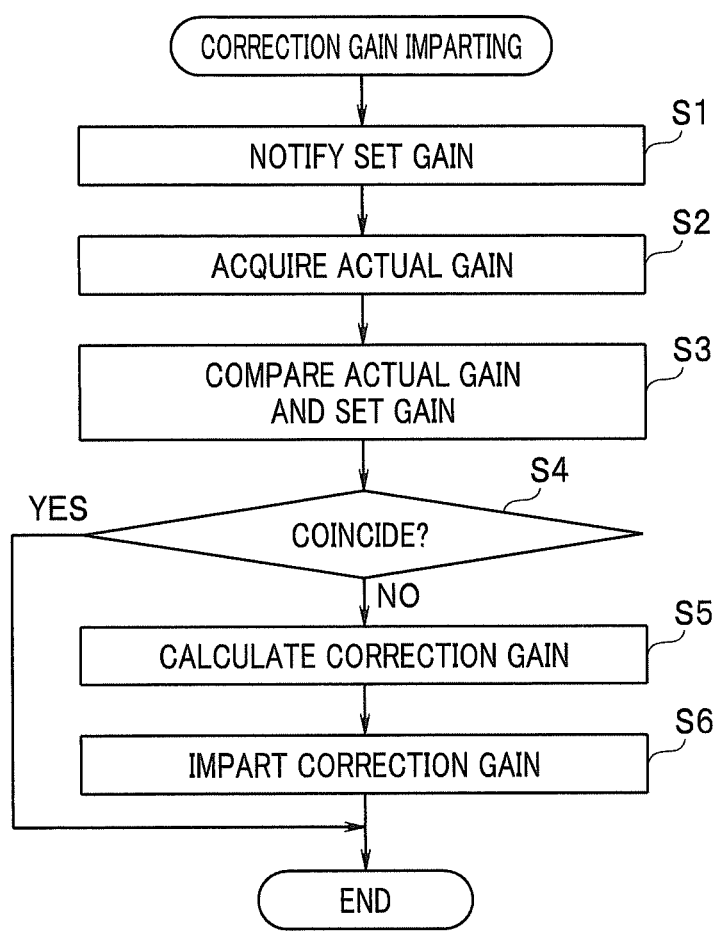
FIG. 5 is a flowchart for explaining operation in the first embodiment.

Operation in the embodiment configured in this way is explained with reference to FIG. 2 to FIG. 5. FIG. 2 is an explanatory diagram for explaining the set gain. FIG. 3 is an explanatory diagram for explaining the actual gain during disturbance occurrence. FIG. 4 is an explanatory diagram showing an example in which the correction gain is imparted during the disturbance occurrence. FIG. 5 is a flowchart for explaining operation in the first embodiment.

It is assumed that the fluorescence observation mode is set. The control section 41 outputs an illumination control signal to the light-source control section 32 of the light source apparatus 3 and instructs the light-source control section 32 to emit illumination light suitable for the fluorescence observation. The light-source control section 32 controls the LED light source 31 to emit the reference light and the excitation light in a time division manner.

FIG. 2 shows emitted light from a light source in this case and shows irradiation of the excitation light, the excitation light, and the reference light on a subject for each one field in a time division manner. In other words, FIG. 2 shows an example in which the excitation light is irradiated on the subject within a period of two fields among three fields and the reference light is irradiated on the subject within a period of the remaining one field.

The emitted light of the light source apparatus 3 is led to the distal end of the insertion section 2a via the light guide 21 and irradiated on a not-shown subject. Return light from the subject is made incident on the photoelectric conversion section 22a of the image pickup device 22 via a not-shown objective lens. The photoelectric conversion section 22a photoelectrically converts an incident optical image and outputs a video signal. In other words, as shown in FIG. 2, in the fluorescence field, fluorescence, which is return light from the subject corresponding to the irradiation of the excitation light, is made incident on the photoelectric conversion section 22a. A video signal based on the fluorescence is supplied to the amplifier 22b. In the background light field, background light, which is return light from the subject corresponding to the irradiation of the reference light, is made incident on the photoelectric conversion section 22a. A video signal based on the background light is supplied to the amplifier 22b.

On the other hand, the control section 41 reads out the set gains set in the fluorescence field and the background light field from the memory 43. In step S1 in FIG. 5, the control section 41 includes information concerning the set gains in field information indicating whether the respective fields are the fluorescence field or the background light field and transmits the information to the image-pickup control section 25. The image-pickup control section 25 transmits a gain control signal to the communication section 22c through digital communication.

Consequently, set gains corresponding to the respective fields are set in the amplifier 22b. The amplifier 22b imparts the set gains to the video signal and outputs the video signal. FIG. 2 shows this state. In FIG. 2, the set gain in the fluorescence field is A and the set gain in the background light field is B. The gain A is set to a value sufficiently larger than the gain B. A video signal based on fluorescence having a relatively small light amount is amplified by the sufficiently large gain A. A video signal based on background light having a relatively large light amount is amplified by the relatively small gain B. Consequently, levels of the video signals in the respective fields outputted from the image pickup device 22 become proper.

The video signal outputted from the image pickup device 22 is supplied to the video receiving section 26. When the image pickup device 22 performs an analog output, the video receiving section 26 removes noise with correlated double sampling processing for the inputted video signal, converts the inputted video signal into a digital signal with analog/digital conversion processing, and thereafter outputs the digital signal to the image processing section 42 of the video processor 4.

When the image pickup device 22 performs a digital output, the video receiving section 26 receives the digital video signal outputted from the image pickup device 22 and outputs the digital video signal to the image processing section 42 of the video processor 4.

The image processing section 42 applies predetermined image signal processing to the inputted video signal and thereafter converts the video signal into a display form suitable for the monitor 5 and outputs the video signal to the monitor 5. Note that the video signal based on the fluorescence and the video signal based on the background light are combined. A fluorescence observation image obtained by combining the fluorescence image and the background light image is displayed on the display screen of the monitor 5. In this way, the fluorescence observation image picked up by the image pickup device 22 can be observed.

It is assumed that the gain control signal transmitted by communication between the image-pickup control section 25 and the amplifier 22b is affected by disturbance and the set gain is not correctly transmitted to the amplifier 22b. FIG. 3 shows an example in this case and shows an example in which the gain A (a hatched part) is set because of disturbance in a predetermined background light field in which the gain B should be originally set.

The gain A is sufficiently large compared with the gain B. The video signal based on the background light having the large light amount is amplified by the large gain A, whereby a level of the video signal based on the background light is extremely large. In other words, in this case, the background image is excessively bright compared with the fluorescence image. The fluorescence observation image is unclear.

Therefore, in the present embodiment, for example, the image pickup device 22 outputs the video signal including the information concerning the actual gain in a blanking period. The video receiving section 26 acquires the information concerning the actual gain from the inputted video signal (step S2). For example, after including the information concerning the actual gain in the blanking period of the video signal, the video receiving section 26 outputs the video signal to the image processing section 42. The image processing section 42 acquires the information concerning the actual gain from the video signal and outputs the information to the control section 41. The control section 41 refers to the memory 43, reads out the set gain, and compares the set gain with the actual gain outputted from the image processing section 42 (step S3). The control section 41 detects whether the set gain and the actual gain coincide with each other (step S4). When the set gain and the actual gain coincide with each other, the control section 41 ends the processing. When the set gain and the actual gain do not coincide with each other, the control section 41 calculates a correction gain based on a difference between the actual gain and the set gain (step S5).

FIG. 4 shows the correction gain calculated in this way. FIG. 4 shows an example in which, because of disturbance, as indicated by hatched parts, the gain A is imparted to the video signal in the background light field and the gain B is imparted to the video signal in the fluorescence field. In this case, the control section 41 generates a correction gain C having an amplification factor smaller than 1 in the background light field to which the gain A is imparted and calculates a correction gain D having an amplification factor larger than 1 in the fluorescence field to which the gain B is imparted.

Note that the correction gain calculated by the control section 41 is a gain corresponding to a difference between the actual gain and the set gain of the amplifier 22b. The same amplification as the amplification performed when the video signal is amplified by the set gain is enabled irrespective of the actual gain by imparting the correction gain to the video signal.

The control section 41 gives the calculated correction gain to the amplifier circuit 42a of the image processing section 42. The amplifier circuit 42a imparts the correction gain to the inputted video signal (step S6). In this way, the video signal in the background light field to which the gain A is imparted is attenuated. The video signal in the fluorescence field to which the gain B is imparted is amplified to be the same appropriate level as the level of the video signal in another field amplified by the set gain in the image pickup device 22.

In other words, even when a gain other than the set gain is imparted in the image pickup device 22 because of disturbance or the like, the video signal is amplified to a proper level using the correction gain in the amplifier circuit 42a of the image processing section 42. Therefore, it is possible to set the brightness of the fluorescence image and the background light image to proper brightness. In this way, even when a correct set gain cannot be set in the image pickup device 22 because of the influence of disturbance or the like, the fluorescence observation image displayed on the monitor 5 can be formed as a clear image.

In this way, in the present embodiment, the actual gains imparted in the respective fields are detected in the image pickup device, the correction gains are calculated by the comparison of the set gains, which should be originally set, and the actual gains in the respective fields, and the correction gains corresponding to the actual gains are imparted to the video signal in a circuit in a post stage of the image pickup device. Consequently, in the present embodiment, even when a gain to be set in the image pickup device is not set because of disturbance or the like, the video signal to which the same gains as the gains to be set in the respective fields are imparted can be obtained. Therefore, for example, even when different gains are set in the fluorescence field and the background light field, the same gains as the gains to be set in the respective fields can be imparted to the video signal irrespective of the influence of the disturbance or the like. It is possible to set the fluorescence image and the background light image to proper brightness and obtain a clear fluorescence observation image.

Modification

Figure 6:
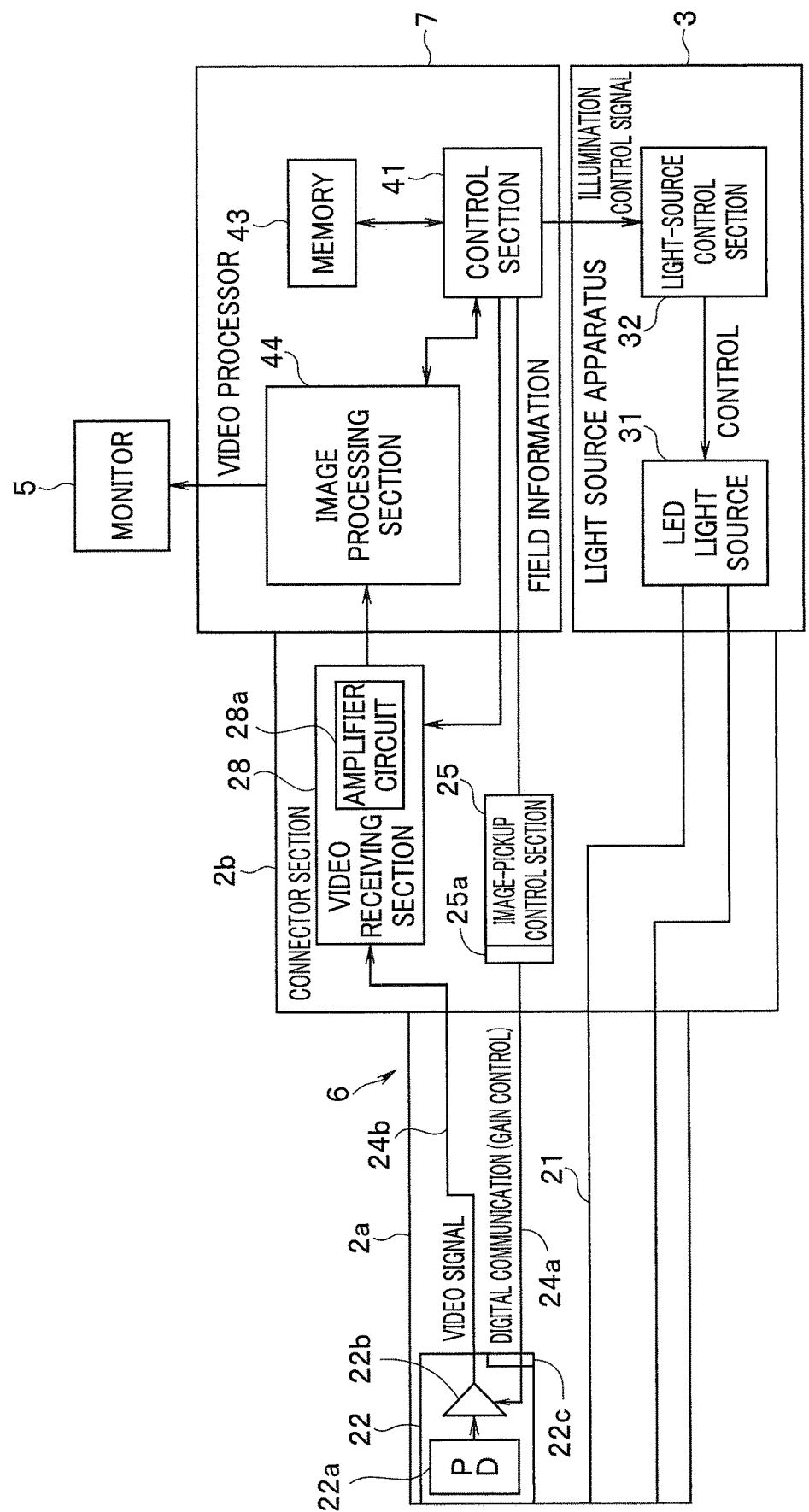
FIG. 6 is a block diagram showing a modification.

FIG. 6 is a block diagram showing a modification. In FIG. 6, the same components as the components shown in FIG. 1 are denoted by the same reference numerals and signs and explanation of the components is omitted. In the present modification, a video processor 7 including an image processing section 44, in which the amplifier circuit 42a is omitted, is adopted, and an endoscope 6 incorporating a video receiving section 28 mounted with an amplifier circuit 28a that imparts a correction gain to the video receiving section 26 in FIG. 1 is adopted.

In the present modification, the control section 41 is configured to supply the information concerning the correction gain to the amplifier circuit 28a. The video receiving section 28 includes an amplifying function by the amplifier circuit 28a besides the same function as the function of the video receiving section 26. The video signal outputted from the image pickup device 22 is amplified by the amplifier circuit 28a using the correction gain according to necessity and thereafter supplied to the image processing section 44 of the video processor 7.

The other components and action effects are the same as those in the embodiment shown in FIG. 1.

Modification

Figure 7:
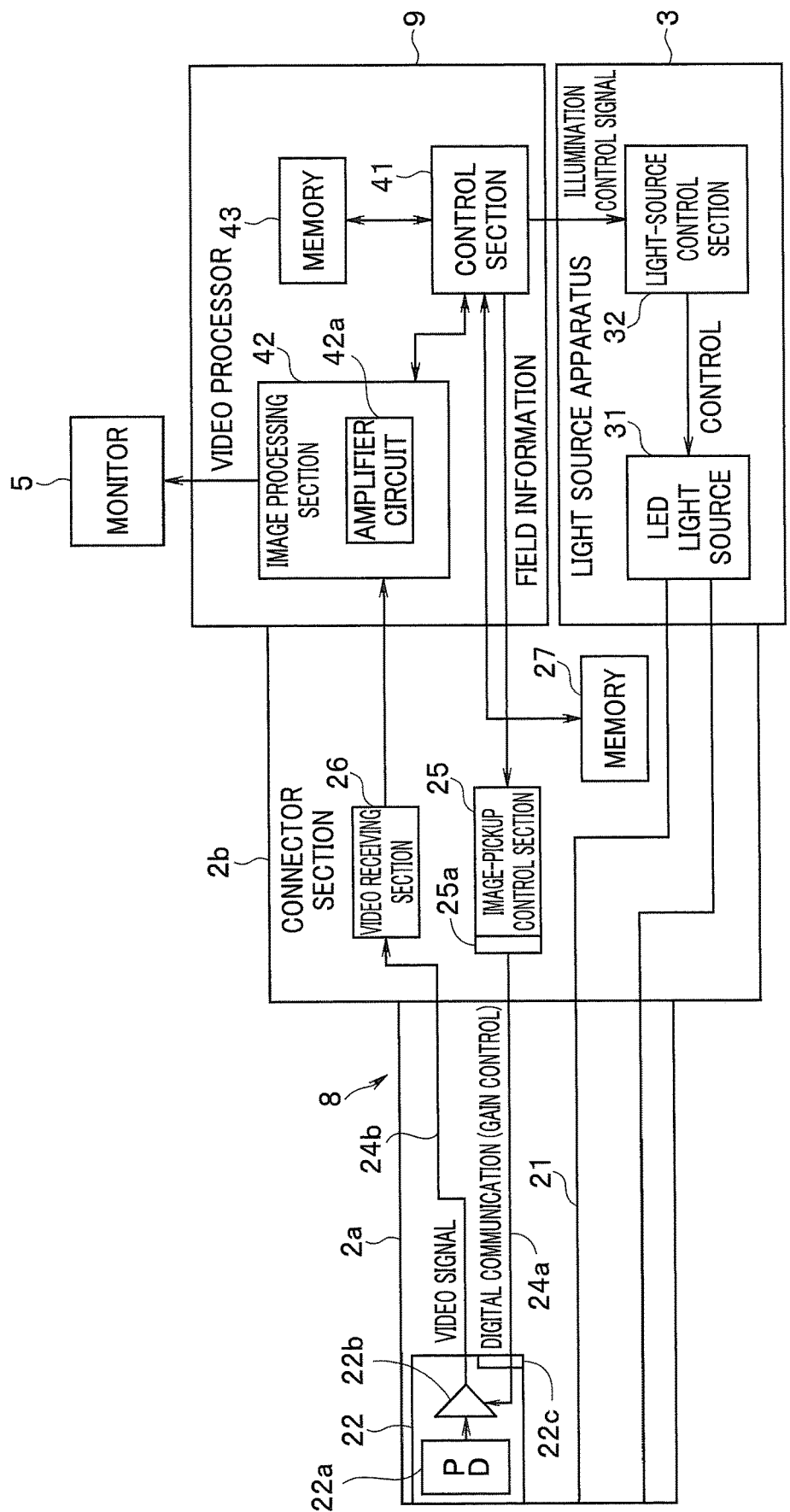
FIG. 7 is a block diagram showing a modification.

FIG. 7 is a block diagram showing a modification. In FIG. 7, the same components as the components shown in FIG. 1 are denoted by the same reference numerals and signs and explanation of the components is omitted. In the present modification, an endoscope 8 incorporating a memory 27 in the connector section 2b is adopted.

The memory 27 stores the same information as the information stored in the memory 43 shown in FIG. 1. The control section 41 is configured to read out the information stored in the memory 27 when the endoscope 8 is connected to a video processor 9 by the connector section 2b. Gain values and gain ratios that should be imparted to the fluorescence field and the background light field are affected by a spectral sensitivity characteristic of the image pickup device 22. Therefore, information concerning a set gain corresponding to the spectral sensitivity characteristic of the image pickup device 22 is stored in the memory 27. For example, even when an endoscope mounted with an image pickup device of a new type not stored in the memory 43 in the video processor 4 shown in FIG. 1 is adopted, information concerning a set gain considering the image pickup device of the new type is stored in the memory 27. An optimum set gain can be set in the image pickup device.

Spectral sensitivity characteristics and the like of an optical system of the endoscope 8 and the image pickup device 22 have individual differences. Therefore, a gain value for absorbing fluctuation of the individual differences can be stored in the memory 27 incorporated in the endoscope 8 as the information concerning the set gain. For example, characteristics of the optical system and the image pickup device may be checked beforehand. The gain value for absorbing the fluctuation of the individual differences may be set according to a result of the check. For example, when an image pickup device having low sensitivity in a fluorescence wavelength is mounted, a gain imparted to a video signal based on fluorescence only has to be set high.

In this way, in the present modification, the gain is set based on the information stored in the memory 27 mounted on the endoscope 8. Consequently, even an endoscope mounted with a new image pickup device is capable of performing stable amplification processing irrespective of an individual difference of each endoscope and can always obtain a clear fluorescence observation image.

Note that FIG. 1 shows an example in which the control section 41 of the video processor 4 includes the information concerning the set gain in the field information and notifies the information to the image-pickup control section 25. However, in the present modification, since the information concerning the set gain is stored in the memory 27, the control section 41 may be configured to notify only field information indicating types of modes and fields to the image-pickup control section 25. In this case, the image-pickup control section 25 only has to read out the set gain from the memory 27 according to the field information and set the set gain in the amplifier 22b.

Second Embodiment

Figure 8:
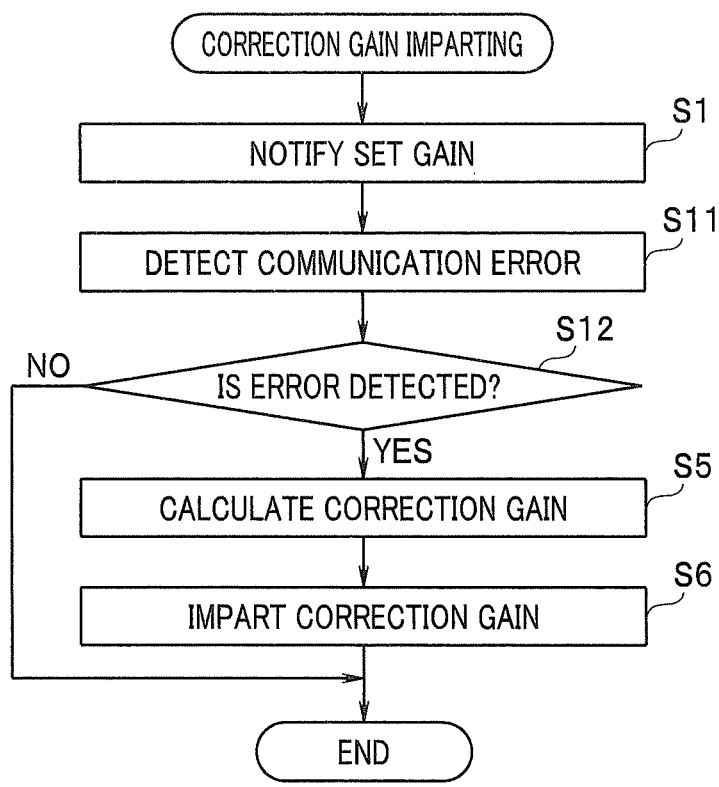
FIG. 8 is a flowchart adopted in a second embodiment of the present invention.

FIG. 8 is a flowchart adopted in a second embodiment of the present invention. A hardware configuration in the present embodiment is the same as the hardware configuration in the first embodiment. In FIG. 8, the same steps as the steps in FIG. 5 are denoted by the same reference signs and explanation of the steps is omitted.

In the example explained in the first embodiment, the endoscope 2 acquires the actual gain and, if necessary, imparts the correction gain to the video signal according to the comparison of the actual gain and the set gain. Inconsistency of the actual gain and the set gain is considered to be because a failure is caused by disturbance or the like in communication performed via the signal line 24a. When the set gain is not notified to the amplifier 22b because of this communication error, the amplifier 22b is considered to impart a set gain, which is imparted to a preceding field before the notification, to the video signal in the next field as well. In other words, if types of a mode and a field during the communication error occurrence are known, a gain that should be imparted can be learned.

Therefore, in the present embodiment, when the communication error occurs, the actual gain is not acquired and a correction gain is calculated from the types of the mode and the field during the communication error occurrence.

The image-pickup control section 25 is performing communication with the communication section 22c of the image pickup device 22 via the signal line 24a and is capable of detecting a communication error with various general methods. For example, the image-pickup control section 25 adds a checksum to the information concerning the set gain to be notified and transmits the information. The communication section 22c detects the communication error using the checksum.

When a communication standard for carrying out a handshake during communication is adopted, the image-pickup control section 25 is capable of detecting a communication error because of a failure in the handshake. For example, there are an I2C (inter-integrated circuit) bus and the like as such a communication standard. It is possible to determine a communication error according to whether ACK (acknowledgement) is returned.

When detecting a communication error through communication with the image pickup device 22, the image-pickup control section 25 outputs information concerning the communication error to the control section 41. Consequently, the control section 41 calculates a correction gain based on a set gain corresponding to types of a mode and a field during the communication error occurrence and a set gain of a preceding field. Note that the correction gain is a known value. The control section 41 can easily calculate the correction gain by storing information concerning the correction gain in the memory 43.

In the embodiment configured in this way, in step S11 in FIG. 8, the image-pickup control section 25 detects a communication error. When detecting occurrence of the communication error, the image-pickup control section 25 transmits information concerning the detection of the occurrence of the communication error to the control section 41. In step S12, the control section 41 determines whether a communication error is detected. When a communication error is not detected, the control section 41 ends the processing. When a communication error is detected, in step S5, the control section 41 calculates a correction gain based on a set gain corresponding to types of a mode and a field during the error occurrence and a set gain of a preceding field.

Other action is the same as the action in the first embodiment.

In this way, in the present embodiment, the same effects as the effects in the first embodiment can be obtained. In the present embodiment, it is unnecessary to calculate the correction gain based on the comparison of the actual gain and the set gain. The correction gain sometimes can be easily calculated and the processing can be simplified.

Third Embodiment

Figure 9:
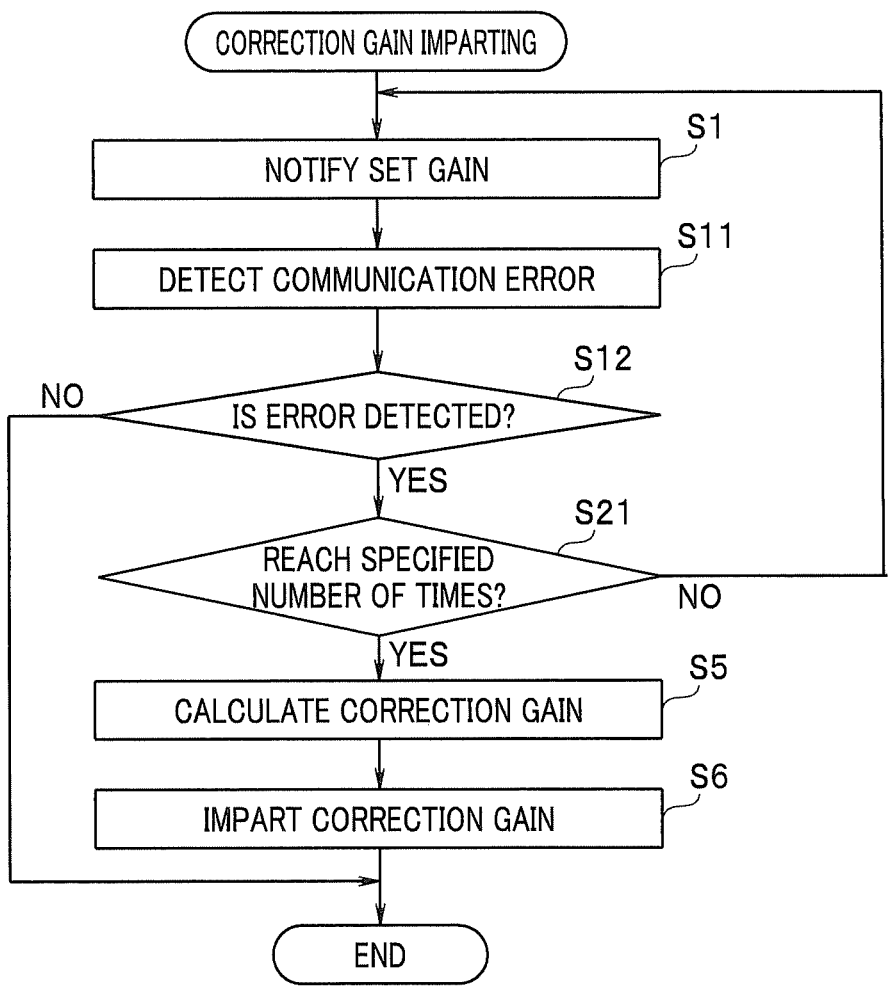
FIG. 9 is a flowchart adopted in a third embodiment of the present invention.

FIG. 9 is a flowchart adopted in a third embodiment of the present invention. A hardware configuration of the present embodiment is the same as the hardware configuration in the first embodiment. In FIG. 9, the same steps as the steps in FIG. 8 are denoted by the same reference signs and explanation of the steps is omitted.

In the first embodiment, the digital gain is added as the correction gain. However, if a positive digital gain is imparted according to the actual gain <the set gain, although the brightness of the fluorescence image and the background image can be set to appropriate brightness, the number of gradations corresponding to the number of bits during A/D conversion decreases by the gain, resolution decreases, and image quality is deteriorated. When the video signal is amplified to a level exceeding an input range of the A/D conversion according to the actual gain >the set gain, information in a portion exceeding the input range cannot be restored even if a negative digital gain is imparted. Therefore, an image quality improvement effect is relatively small. Note that, even in this case, the imparting of the negative digital gain has an effect of preventing an image of another field from becoming unclear because a pertinent field is too bright.

In this way, when the digital gain is imparted as the correction gain, a problem such as the image quality deterioration occurs. Therefore, in the present embodiment, when a communication error occurs, the set gain is set in the amplifier 22b by retransmitting a gain control signal for designating the set gain. When the communication error cannot be avoided by the retransmission, the imparting of the correction gain in the first and second embodiments is performed.

An example shown in FIG. 9 is different from the flow of FIG. 8 in that, when it is determined in step S12 that a communication error is detected, the processing shifts to step S5 through step S21. When determining in step S12 that a communication error has occurred, in step S21, the image-pickup control section 25 determines whether the number of times of transmission of the set gain has reached a specified number of times. When the number of times of transmission of the set gain has not reached the specified number of times, the image-pickup control section 25 returns the processing to step S1 and retransmits the information concerning the set gain to the communication section 22c with the gain control signal. If the set gain is correctly set in the amplifier 22b by this retransmission, the image-pickup control section 25 determines in step S12 that an error is not detected and ends the processing.

If a communication error is caused by the retransmission as well, in step S21, the image-pickup control section 25 determines whether the number of times of transmission of the set gain has reached the specified number of times. If the number of times of transmission reaches the specified number of times, the image-pickup control section 25 shifts the processing to step S5 and calculates a correction gain.

Other action is the same as the action in the first and second embodiments.

In this way, in the present embodiment, when a communication error occurs, the information concerning the set gain is retransmitted to set a correct set gain in the image pickup device. Only when the set gain cannot be correctly set in the image pickup device even by the retransmission, the correction gain is imparted. If the correct set gain can be set by the retransmission, it is possible to set brightness of images in the respective fields to optimum brightness without involving image quality deterioration.

Note that FIG. 9 shows an example in which the gain control signal for designating the set gain is retransmitted during the occurrence of the communication error. However, the gain control signal for designating the set gain may be retransmitted when the actual gain is detected and the actual gain and the set gain do not coincide with each other.

The image processing section 42 may not only impart the correction gain but also change parameters of image processing such as noise reduction and further reduce a deterioration degree of image quality according to the correction gain.

Further, the present invention is not limited to the embodiments explained above per se. In an implementation stage, the constituent elements can be modified and embodied in a range not departing from the gist of the present invention. Various inventions can be formed by appropriate combinations of the plurality of constituent elements disclosed in the embodiments. For example, several constituent elements may be deleted from all the constituent elements explained in the embodiments.

What is claimed is:

1. An image pickup system comprising:
   an image pickup device comprising:
     an image sensor configured to pick up an image of an object and output a video signal;
     a first amplifier circuit configured to amplify and output the video signal of at least one of a plurality of fields; and
     a communication circuit configured to acquire, through communication with an outside of the image pickup system, a set gain to be set as a gain of the first amplifier circuit;
   an image-pickup control circuit configured to transmit, through communication with the communication circuit, the set gain of at least one of the plurality of fields to the image pickup device;
   a second amplifier circuit configured to amplify the video signal outputted from the image pickup device; and
   a processor,
   wherein the image-pickup control circuit or the processor is configured to detect whether the video signal is amplified by the set gain in the first amplifier circuit, and
   wherein the image-pickup control circuit or the processor is configured to calculate, according to a result of the detection indicating that the video signal is not amplified by the set gain in the first amplifier circuit, a correction gain set in the second amplifier circuit.

2. The image pickup system according to claim 1, wherein the image-pickup control circuit or the processor is configured to acquire, as an actual gain, a gain imparted to the video signal by the first amplifier circuit and obtain the result of the detection according to comparison of the set gain and the actual gain.

3. The image pickup system according to claim 1, wherein the image-pickup control circuit or the processor is configured to obtain the result of the detection by detecting a communication error between the image-pickup control circuit and the communication circuit.

4. The image pickup system according to claim 2, wherein the image-pickup control circuit or the processor is configured to obtain the correction gain based on a difference between the actual gain and the set gain.

5. The image pickup system according to claim 1, wherein the image-pickup control circuit or the processor is configured to obtain the correction gain based on information concerning one field of the plurality of fields in which the video signal is not amplified by the set gain and information concerning a preceding field of the one field.

6. The image pickup system according to claim 1, wherein, when the result of the detection is obtained, the image-pickup control circuit is configured to retransmit of the set gain to the image pickup device, and
   wherein, when the result of the detection has reached a specified number of times, the image-pickup control circuit is configured to calculate the correction gain.

7. An endoscope system comprising:
   an endoscope;
   a light source apparatus configured to irradiate illumination light on an object, the illumination light having two or more kinds of light, each with a different wavelength band and assigned to a respective field of a plurality of fields;
an image pickup device comprising:
  an image sensor provided in the endoscope and configured to pick up an image of the object and output a video signal;
  a first amplifier circuit configured to amplify and output the video signal of at least one of the plurality of fields; and
  a communication circuit configured to acquire, through communication with an outside of the endoscope, a set gain to be set as a gain of the first amplifier circuit;
a video processor configured to perform image processing on the video signal outputted from the endoscope;
an image-pickup control circuit configured to transmit, through communication with the communication circuit, the set gain of at least one of the plurality of fields to the image pickup device;
a second amplifier circuit configured to amplify the video signal outputted from the image pickup device; and
a processor,
wherein the image-pickup control circuit or the processor is configured to detect whether the video signal is amplified by the set gain in the first amplifier circuit, and
wherein the image-pickup control circuit or the processor is configured to calculate, according to a result of the detection indicating that the video signal is not amplified by the set gain in the first amplifier circuit, a correction gain set in the second amplifier circuit.

8. The endoscope system according to claim 7, further comprising a memory provided in the endoscope and configured to store information concerning the set gain of at least one of the plurality of fields.

9. The endoscope system according to claim 7,
wherein the image-pickup control circuit is provided in the endoscope.

10. The endoscope system according to claim 7,
wherein the second amplifier circuit is configured to impart a digital gain to a digital video signal outputted from the endoscope.

11. The endoscope system according to claim 7,
wherein the image-pickup control circuit or the processor is configured to:
  acquire, as an actual gain, a gain imparted to the video signal by the first amplifier circuit; and
  obtain the result of the detection according to comparison of the set gain and the actual gain or obtain the result of the detection by detecting a communication error between the image-pickup control circuit and the communication circuit.

12. An image-pickup gain setting method for an image pickup system,
wherein the image pickup system comprises:
  an image pickup device comprising:
    an image sensor configured to pick up an image of an object and output a video signal;
    a first amplifier circuit configured to amplify and output the video signal of at least one of a plurality of fields; and
    a communication circuit configured to acquire, through communication with an outside of the image pickup system, a set gain to be set as a gain of the first amplifier circuit;
  an image-pickup control circuit configured to transmit, through communication with the communication circuit, the set gain of at least one of the plurality of fields to the image pickup device; and
  a second amplifier circuit configured to amplify the video signal outputted from the image pickup device, and
wherein the image-pickup gain setting method comprises:
  setting, in the first amplifier circuit, the set gain of at least one of the plurality of fields transmitted from the image-pickup control circuit to the communication circuit;
  acquiring an actual gain of the first amplifier circuit based on the video signal outputted from the image pickup device;
  comparing the set gain and the actual gain to thereby detect whether the video signal is amplified by the set gain in the first amplifier circuit;
  calculating, when a result of the detection indicating that the video signal is not amplified by the set gain in the first amplifier circuit is obtained by the set gain and the actual gain not coinciding with each other, a correction gain based on a difference between the actual gain and the set gain; and
  setting the correction gain in the second amplifier circuit.

* * * * *